United States Patent [19]

Sama

[11] Patent Number: 4,762,620
[45] Date of Patent: Aug. 9, 1988

[54] METHOD AND APPARATUS FOR MEASURING THE QUANTITY OF PLASMA WATER REMOVED DURING HEMODIALYSIS

[75] Inventor: Claudio Sama, Brescello, Italy
[73] Assignee: Inphardial S.p.A., Italy
[21] Appl. No.: 17,252
[22] PCT Filed: May 6, 1986
[86] PCT No.: PCT/EP86/00286
    § 371 Date: Dec. 9, 1986
    § 102(e) Date: Dec. 9, 1986
[87] PCT Pub. No.: WO86/06637
    PCT Pub. Date: Nov. 20, 1986

[30] Foreign Application Priority Data
    May 10, 1985 [IT] Italy .................. 20648 A/85

[51] Int. Cl.⁴ .................. B01D 13/00; B01D 13/01
[52] U.S. Cl. .................. 210/646; 210/87; 210/94; 210/321.71; 210/929
[58] Field of Search .................. 210/929, 87, 94, 95, 210/321.3, 646, 321.71

[56] References Cited

U.S. PATENT DOCUMENTS

| | | | |
|---|---|---|---|
| 3,990,973 | 11/1976 | Boag et al. | 210/929 |
| 4,212,744 | 7/1980 | Oota | 210/321.3 |
| 4,218,313 | 8/1980 | Aid et al. | 210/929 |
| 4,496,458 | 1/1985 | Lee | 210/90 |
| 4,610,782 | 9/1986 | Tersteegen et al. | 210/929 |

FOREIGN PATENT DOCUMENTS 2014060 2/1979 United Kingdom.

Primary Examiner—Benoit Castel
Attorney, Agent, or Firm—Steele, Gould & Fried

[57] ABSTRACT

A graduated container (1) is connected both to a filtering compartment (10) of a dialyzer (9) and to the dialysis liquid circuit (8); the connection between the graduated container and the dialyzing liquid circuit being made through a chamber (2) into which extends a tube (6) connected to the dialyzing liquid circuit (8).

9 Claims, 2 Drawing Sheets

METHOD AND APPARATUS FOR MEASURING THE QUANTITY OF PLASMA WATER REMOVED DURING HEMODIALYSIS

BACKGROUND OF THE INVENTION

This invention relates to a device for measuring the quantity of plasma water removed during an extracorporeal dialysis sitting.

More particularly, this device consists of a graduated container having means for connecting it to a filtering compartment of a dialyzer and other means for connecting it to the dialysis liquid circuit and is characterized in that the connection between the graduated container and the dialysis liquid circuit is made through a chamber into which extends a tube connected to the dialysis liquid circuit.

The type of dialyzer suited for the purpose is already known and is described in Italian Patent Application No. 21947 A/81. It comprises basically two bundles of hollow fibres housed in two hydraulically separated compartments. The blood of the patient subjected to dialysis flows inside each of the fibres of both bundles. The outer walls of the hollow fibres with semipermeable membranes of one of the two bundles, which is considerably bigger than the other, are in contact with the dialyzing liquid, and the compartment which contains them is connected to the dialyzing liquid circuit. The outer walls of the hollow fibres of the second bundle are not flowed over by the dialyzing liquid. The first compartment thus performs a dialyzing and purifying action while the second performs a filtering action. Depending on the type of filtration desired the type of hollow fibre of the second bundle may thus be the same as or different from that of the first bundle.

It is known that extracorporeal dialysis has the principal purpose of removing from the patients's blood a certain quantity of plasma water, urea and various metabolites.

When the quantity of plasma water removed is too great the patient is subject to various complications such as for example cramps and collapse. When it is insufficient no important effect occurs immediately but after two or three dialysis sittings the characteristic symptoms of renal insufficiency appear.

At the same time the majority of currently used dialyzers are not equipped with any device to measure the quantity of water progressively removed during the dialysis sitting. Furthermore with the same dialyzer and the same operational conditions the quantity of plasma water removed during a dialysis sitting varies from one patient to another. Under these conditions the operator who starts to subject a patient to extracorporeal dialysis regulates roughly in advance the pressure of the dialysis liquid and the venous pressure on the basis of the characteristics of the dialyzer and the quantity of water which is to be removed from the patient. After the dialysis sitting he determines the quantity of water really removed, verifying the drop in the patient's body weight.

Time by time the operator allows for the results obtained in the course of previous sittings to seek to determine the optimal operating conditions for each patient. This empirical method does not however secure satisfactory results because a certain number of variables involved escape his control. One of these variables is the hydraulic permeability of the semipermeable membranes of which the dialyzer is made and which, manufacturers being equal, has in the best of cases a variability on the order of ±10% but fairly often is near ±20%. Another variable is the patient's condition, which changes with change in diet and many other factors which escape even the most diligent operator.

To avoid these and other drawbacks known to those skilled in the art, in the course of recent years the bed scales has been used on which the patient subject to a dialysis sitting is placed and which makes it possible to determine weight loss and hence the quantity of plasma water removed progressively as the dialysis proceeds.

But neither is the bed scale free from drawbacks such as for example the very high cost thereof and the fact that during the dialysis sitting the patient usually takes liquids and/or food which prevent the operator's determining exactly the quantity of plasma water removed.

In recent years it has also been proposed to equip dialysis machines with volumetric control systems which would make it possible to determine the difference between the volume of the dialyzing liquid which enters the dialyzer and of that which issues therefrom. This system also presents the drawback of high cost; furthermore the majority of dialysis machines currently in use are not equipped with such systems and the problem of how to determine the quantity of plasma water removed with such machines remains unsolved.

SUMMARY OF THE INVENTION

An object of this invention is therefore an economical, simple and effective device for determining progressively while the extracorporeal dialysis proceeds the quantity of plasma water removed.

This is accomplished by a device comprising a graduated container and connections connecting it both to a filtering compartment of a dialyzer and to the dialysis liquid circuit, the connection between the graduated container and the dialysis circuit being made in such a manner that the pressure of the graduated container is always the same as that of the dialysis liquid coming out of the dialyzer so that the dialyzing liquid does not flow into the graduated container while it can freely enter the filtrate wich issues from the filtering compartment of the dialyzer.

Other features and advantages of the device according to this invention will become clear from the following detailed description of two possible practical embodiments thereof illustrated as nonlimiting examples in the annexed figures in which is shown a longitudinal section thereof.

DESCRIPTION OF THE PREFERRED EMBODIMENTS

Figure 1:
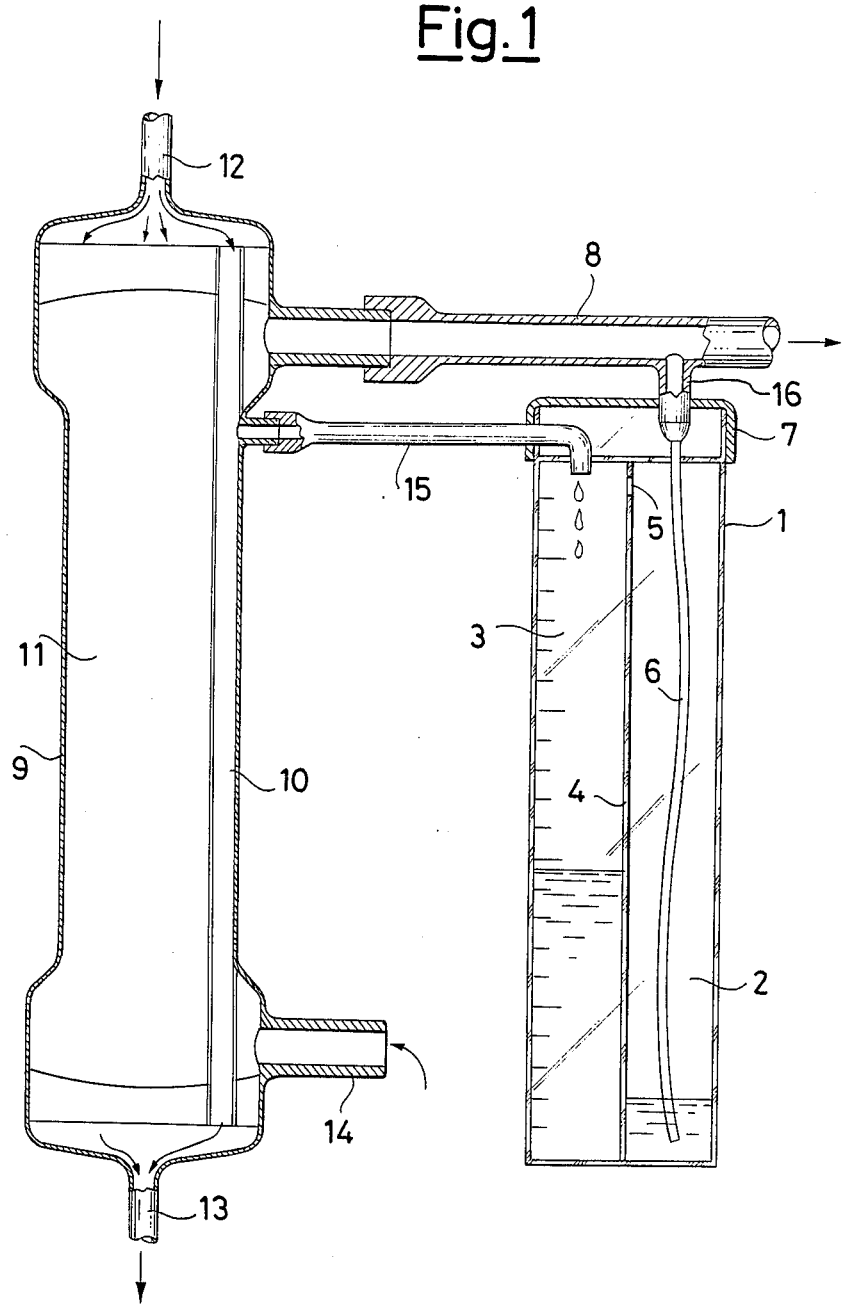
FIG. 1 is a section view through a first embodiment of the invention.
Figure 2:
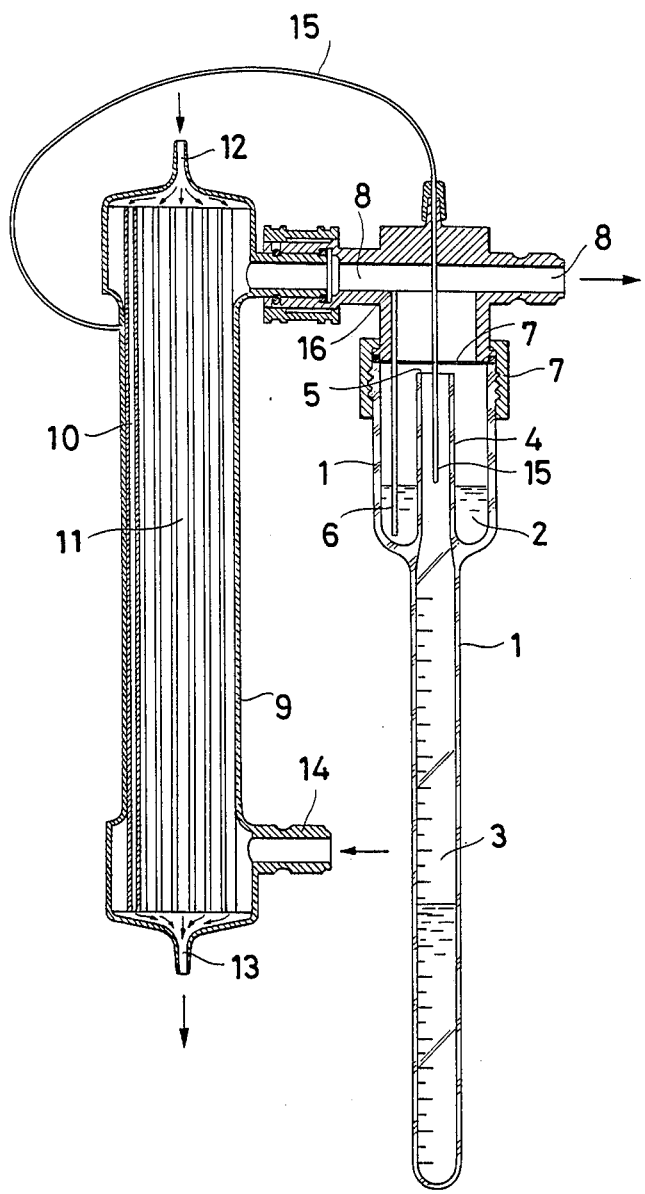
FIG. 2 is a section view of an alternative embodiment of the invention.

As illustrated in the FIGS. 1 and 2, the device according to this invention consists of a container 1 divided in two communicating chambers 2 and 3 through a hole or an opening 5 made in the dividing wall 4 and is closed by a tight cover 7 which is traversed in a tight manner by a branch 16 of the connecting tube 8 which connects the dialyzer with the suction pump, said branch 16 being fitted with a tube 6 which extends into the chamber 2. Furthermore the cover 7 is traversed by a tube 15 which connects the second chamber 3 with a hose connection leading from the filtering compartment 10 of the dialyzer 9.

The dialyzer 9 is illustrated summarily in the figures because it is not an object of this invention and is described in Italian Patent Application No. 21947 A/81.

The container 1 is connected to a dialyzer 9 which is divided in a filtering compartment (10) and a dialyzing compartment (11) both containing the same type of hollow fibres with semipermeable membrane preferably belonging to the same manufacturing lot. The filtering compartment 10 being significantly smaller than the dialyzing compartment 11 and containing a very small but accurately known number of hollow fibres, e.g. less than 5% of the number of hollow fibres contained in the dialyzing compartment.

During operation the patient's blood reaches the hose connection 12 of the dialyzer 9 and is distributed proportionally between the hollow semipermeable membrane fibres contained in the dialyzing compartment 11 and those contained in the filtering compartment 10 and issues from the hose fitting 13. The dialyzing liquid in turn enters the hose fitting 14, flows through the interstices existing between the hollow fibres which are located in the compartment 11 and is conveyed through the tube 8 to the suction pump (not shown).

The blood which flows along the hollow semipermeable membrane fibres located in the chamber 10 is filtered losing a quantity of plasma water proportionate to the transmembrane pressure and a percentage representative of the water removed from the blood of the patient through the hollow fibres of the dialyzing compartment 11. The tube 6 connected through the branch 16 to the suction pump circuit has the purpose of maintaining in the chambers 2 and 3 of the container 1 the same pressure as the dialysis liquid wich issues from the dialyzer and thus aid downflow of the filtrate through the tube 15 from the compartment 10 to the graduated chamber 3.

At least the graduated chamber but preferably all of container 1 consists of a rigid transparent material such as for example glass or suitable polymeric resin. The operator can thus read the quantity of filtrate which downflows from 10 to 3 as the dialysis proceeds and find by means of a very simple calculation the quantity of water which has been removed from the patient. For example, if the number of hollow semipermeable membrane fibres contained in the filtering chamber 10 is equal to 5% of the fibres contained in the chamber 10 it is only necessary to multiply by twenty the quantity of liquid caught in 3 to know the quantity of water removed up to that moment from the patient's body. For a more accurate calculation the manufacturer will provide the operator with the possible correction coefficient or the scale of the graduated chamber 3 can be represented in such a manner as to allow for the multiplication factor and thus indicate the quantity of water removed.

From the foregoing description it appears clearly that the device according to this invention provides an extremely simple and reliable solution for such a complex and deeply felt problem as monitoring by the fact that the graduated chamber 3 always has the same pressure as the filtering chamber 10 without requiring the operator's attention and by the fact that the device according to the present invention is made up exclusively of static members and is thus not subject to failure.

Many are the structural variations which can be made to the device illustrated in the figures. It can be made as an accessory of the dialyzer or be incorporated in the dialyzer itself. The two chambers 2 and 3 can be made in the same container or consist of two separate containers connected together by a tube which performs the same function as a hole 5 described above. The form of the chambers 2 and 3 can be the same or different and their cross section can be semicircular, circular, square or of any other form. The tube 6 instead of extending into the chamber 2 can be immersed in a small sack consisting of a flexible film which transmits the pressure variations to the chamber 2 by inflating or deflating.

Other construction or structural modifications may be made without departing from the scope of the present invention.

I claim:

1. A device for measuring a quantity of filtrate removed from a patient during hemodialysis, the filtrate being removed in a dialyzer upon passage of the filtrate from blood of the patient through a semipermeable membrane in a compartment, the compartment defining means for carrying a flow of dialyzing liquid along one side of the semipermeable membrane, and means for carrying a portion of the blood along an opposite side of the semipermeable membrane, a quantity of filtrate passing during dialysis from the portion of the blood to the dialyzing liquid, said device comprising:

a second compartment operable as a filtering chamber, the second compartment also having a semipermeable membrane and means for carrying a portion of the blood along a side of the semipermeable membrane of the second compartment; and, a graduated container connected to the filtering chamber at an opposite side of the semipermeable membrane from the blood, a quantity of filtrate passing during dialysis from the blood to the graduated container and accumulating therein, the quantity of filtrate accumulating in the graduated container being related to the quantity of filtrate removed from the blood and passing to the dialyzing liquid, whereby a total volume of filtrate removed from the blood is indicated by the graduated cylinder, said dialyzer defining a dialysis liquid path and a blood path, the graduated container also being fluidly connected to the dialysis liquid path, whereby the filtering chamber operates at equal pressure with the dialyzer.

2. The device of claim 1, wherein the semipermeable membranes are hollow tubes, the hollow tubes separating the dialyzing liquid from the blood in the dialyzer and separating the blood from a tube leading to the graduated container in the filtering chamber.

3. The device of claim 1, wherein the semipermeable membranes of the dialyzer and of the filtering chamber are hollow tubes carrying blood and are disposed in parallel along a flowpath for the blood, the dialyzer and the filtering chamber being hydraulically separate and fluidly connected such that the filtering chamber and the dialyzer operate at equal pressures.

4. The device of claim 3, wherein the dialyzer and the filtering chamber are disposed in a single subdivided housing and are connected together by an opening across a dividing wall between the dialyzer and the filtering chamber.

5. The device of claim 3, wherein the hollow tubes of the filtering chamber remove about five percent as much filtrate as the dialyzer.

6. A device for measuring a quantity of plasma water removed from a patient's blood during a dialysis sitting by means of a dialyzer (9) having a dialyzing compartment (11), the device comprising:
- a filtering compartment (10) hydraulically separate from the dialyzing compartment (11);
- a graduated container (1) subdivided into two chambers (2, 3) communicating with one another through an opening (5) defined in a dividing wall (4) between said two chambers, the graduated container (1) being closed by a cover (7) traversed
  (i) by a branch (16) of a tube (8) connecting the dialyzing compartment (11) of the dialyzer (9) to a suction means, said branch (16) being fitted with a tube (6) extending into one (2) of said two chambers (2, 3); and,
  (ii) by a tube (15) connecting another (3) of said two chambers (2, 3) with the filtering compartment (10) of the dialyzer (9), whereby the filtering compartment and the dialyzing compartment operate at equal pressure.

7. A method for measuring a quantity of plasma water removed from a patient's blood during a dialysis sitting, the dialysis sitting including passing the blood through a dialysis chamber along a semipermeable membrane with a dialysis liquid disposed on an opposite side of the semipermeable membrane from the blood and controlling pressures of the blood and the dialysis liquid, respectively, filtrate being thereby passed from the blood into the dialysis liquid and being carried away, the method comprising the steps of:
- connecting a filtering chamber in parallel with the dialysis chamber, the filtering chamber also having a semipermeable membrane along one side of which the blood is passed;
- collecting in a graduated container filtrate passing through the semipermeable membrane of the filtering chamber, a quantity of said filtrate as collected indicating a quantity of filtrate passed in the dialysis chamber from the blood to the dialysis liquid; and,
- operating the filtering chamber and the dialysis chamber at equal pressures by connecting both said chambers to a common blood supply and pressurizing the graduated container at a pressure equal to that of the dialysis liquid.

8. The method of claim 7, comprising connecting the graduated container to a conduit carrying the dialysis liquid by a tube.

9. The method of claim 7, comprising connecting the graduated container to a conduit carrying the dialysis liquid by a hole in the graduated container leading to a compartment connected by a tube to the conduit carrying the dialysis liquid.

* * * * *

UNITED STATES PATENT AND TRADEMARK OFFICE
CERTIFICATE OF CORRECTION

PATENT NO. : 4,762,620

DATED : August 9, 1988

INVENTOR(S) : Sama

It is certified that error appears in the above-identified patent and that said Letters Patent is hereby corrected as shown below:

Column 2, line 43, delete "wich" and insert --which--.

Column 4, line 7, delete "a" and insert --the--.

Signed and Sealed this

Twenty-eighth Day of November 1989

Attest:

JEFFREY M. SAMUELS

Attesting Officer     Acting Commissioner of Patents and Trademarks